US012746525B2

(12) United States Patent
Back et al.

(10) Patent No.: US 12,746,525 B2
(45) Date of Patent: Sep. 29, 2026

(54) 1-METHYLCYCLOPROPENE GENERATION APPARATUS

(71) Applicant: ECOPLANTS CO., LTD., Yongin-si (KR)

(72) Inventors: Jung Min Back, Seongnam-si (KR); Eun Sik Choi, Suwon-si (KR)

(73) Assignee: ECOPLANTS CO., LTD., Yongin-si (KR)

( * ) Notice: Subject to any disclaimer, the term of this patent is extended or adjusted under 35 U.S.C. 154(b) by 835 days.

(21) Appl. No.: 18/032,303

(22) PCT Filed: Mar. 27, 2021

(86) PCT No.: PCT/KR2021/003805
§ 371 (c)(1),
(2) Date: Apr. 17, 2023

(87) PCT Pub. No.: WO2022/097849
PCT Pub. Date: May 12, 2022

(65) Prior Publication Data

US 2023/0390728 A1 Dec. 7, 2023

(30) Foreign Application Priority Data

Nov. 5, 2020 (KR) ........................ 10-2020-0146455

(51) Int. Cl.
*B01J 19/18* (2006.01)
*B01J 4/00* (2006.01)
(Continued)

(52) U.S. Cl.
CPC ............... *B01J 19/18* (2013.01); *B01J 4/001* (2013.01); *B01J 19/0033* (2013.01);
(Continued)

(58) Field of Classification Search
CPC ....... B01J 4/00; B01J 4/001; B01J 7/00; B01J 19/00; B01J 19/0006; B01J 19/0033;
(Continued)

(56) References Cited

U.S. PATENT DOCUMENTS 9,992,995 B2 * 6/2018 Ghosh ...................... A23B 9/18
2019/0166861 A1 * 6/2019 Felicetti ................. A23B 7/152
(Continued)

FOREIGN PATENT DOCUMENTS

KR 10-0823872 B1 4/2008
KR 10-2013-0068710 A 6/2013
(Continued)

OTHER PUBLICATIONS

CN 101874998 A with machine translation (Year: 2010).*
KR 101550014 B1 with machine translation (Year: 2015).*
International Search Report mailed Feb. 18, 2022, issued to International Application No. PCT/KR2021/003805.

*Primary Examiner* — Natasha E Young
(74) *Attorney, Agent, or Firm* — Stein IP, LLC

(57) ABSTRACT

A 1-methylcyclopropene generation apparatus according to one embodiment of the present invention comprises: a container comprising a 1-MCP precursor and a reaction solution, and having a pair of through-holes formed in the upper part thereof; a main body comprising an accommodation space for accommodating the container; and a cap coupled to the upper part of the main body in a state in which the container is accommodated in the accommodation space of the main body, wherein the cap comprises an upper frame, a lower frame, a first tube and a second tube, and the lower frame comprises a pair of first tube connection terminals arranged at one side and the other side, and a pair of second tube connection terminals arranged between the pair of first tube connection terminals.

10 Claims, 6 Drawing Sheets

(51) Int. Cl.
*B01J 19/00* (2006.01)
*C07C 13/04* (2006.01)

(52) U.S. Cl.
CPC ....... *B01J 19/0066* (2013.01); *B01J 19/0073* (2013.01); *C07C 13/04* (2013.01)

(58) Field of Classification Search
CPC ................ B01J 19/0053; B01J 19/0066; B01J 19/0073; B01J 19/18; B01J 2219/00; B01J 2219/18; B01J 2219/185; B01J 2219/19; B01J 2219/192; B01J 2219/1923; C07C 13/00; C07C 13/02; C07C 13/04; C07C 2601/00; C07C 2601/06; C07C 2601/10; C07F 7/00; C07F 7/02; C07F 7/08
See application file for complete search history.

(56) References Cited

U.S. PATENT DOCUMENTS

| | | | | |
|---|---|---|---|---|
| 2020/0139340 | A1* | 5/2020 | Schotsmans | B01J 19/245 |
| 2020/0346839 | A1* | 11/2020 | Lee | B67D 3/0041 |

FOREIGN PATENT DOCUMENTS

| | | | |
|---|---|---|---|
| KR | 10-2016-0062059 | A | 6/2016 |
| KR | 10-1747210 | B1 | 6/2017 |
| KR | 10-1877419 | B1 | 7/2018 |
| KR | 10-2372431 | B1 | 3/2022 |
| WO | WO 2018/234424 | A1 | 12/2018 |

* cited by examiner

1-METHYLCYCLOPROPENE GENERATION APPARATUS

CROSS-REFERENCE TO RELATED APPLICATIONS

This application is a national stage of International Application No. PCT/KR2021/003805, now WO 2022/097849, filed Mar. 27, 2021, which claims the benefit of Korean Application No. 10-2020-0146455, filed Nov. 5, 2020, in the Korean Intellectual Property Office, the disclosures of which are incorporated herein by reference.

TECHNICAL FIELD

The present invention relates to a 1-methylcyclopropene generation apparatus, and more particularly, to a 1-methylcyclopropene generation apparatus which may be conveniently used in a storehouse in which agricultural products are stored.

BACKGROUND ART

Cyclopropene derivatives including as 1-methylcyclopropene are substances inhibiting an action of ethylene, which is a plant hormone promoting a ripening process of fruits, flowers, or vegetables, and are known to have excellent effects.

In particular, since 1-MCP is present in a gas phase at room temperature, the inside of a storage warehouse for agricultural products may be easily treated with the 1-MCP. However, since cyclopropene compounds including 1-MCP are prone to polymerization, it may be difficult to store the cyclopropene compounds for a long period of time using a general method.

To address such an issue, Korean Patent Registration No. 10-18977419 discloses an apparatus for easily and directly generating 1-methylcyclopropene in a desired location using a carrier gas by preparing a first container and a second container.

However, such a prior art should develop an apparatus into which two or three containers are inserted, resulting in manufacturing and use inconveniences such as an increase in weight and volume of the apparatus and correct insertion of each container into the apparatus.

PRIOR ART DOCUMENT

Patent Document

Korean Patent Registration No. 10-18977419 (Jul. 7, 2018)

DISCLOSURE OF THE INVENTION

Technical Problem

An object of the present invention is to provide a 1-methylcyclopropene generation apparatus including a main body in which a single container is mounted.

Another object of the present invention is to provide a 1-methylcyclopropene generation apparatus having a simple structure in which a cap is simply coupled to and separated from the main body.

The objects of the present invention are not limited to the above-described objects, and other objects not described will be more clearly understood by those skilled in the art from the following description.

Technical Solution

A 1-methylcyclopropene generation apparatus according to an embodiment of the present invention includes a container, a 1-methylcyclopropene (1-MCP) precursor, and a reaction solution, reacting with the 1-methylcyclopropene precursor to generate 1-methylcyclopropene, therein and having a pair of through-holes formed on an upper portion thereof, a main body having an accommodation space for accommodating the container, and a cap coupled to the upper portion of the main body in a state in which the container is accommodated in the accommodation space of the main body, wherein a recess region for accommodating a portion of the cap is formed in the upper portion of the main body, and a discharge terminal and an introduction terminal protruding upwardly are formed in the recess region, the cap includes an upper frame, a lower frame, and a first tube and a second tube disposed between the upper frame and the lower frame, the lower frame includes a pair of first tube connection terminals, disposed on one side and the other side, and a pair of second tube connection terminals disposed between the pair of first tube connection terminals, upper portions of the pair of first tube connection terminals are connected to one side of the first tube and one side of the second tube, upper portions of the pair of second tube connection terminals are connected to the other side of the first tube and the other side of the second tube, lower portions of the pair of first tube connection terminals are connected to the discharge terminal and the introduction terminal, respectively, the lower portions of the pair of second tube connection terminals are connected to the pair of through-holes, respectively, the introduction terminal is connected to a discharge hole formed in an outer side of the main body, and the 1-methylcyclopropene generation apparatus includes a control unit configured to discharge a carrier gas to the discharge terminal to discharge a reactant, including the 1-methylcyclopropene generated in the container, through the discharge hole.

In the 1-methylcyclopropene generation apparatus according to an embodiment of the present invention, complementary coupling elements may be formed at the lower frame of the cap and the recess region of the main body such that the lower frame is accommodated in the recess region to be stably coupled thereto.

In the 1-methylcyclopropene generation apparatus according to an embodiment of the present invention, a pair of through-holes may be formed in a side surface of the lower frame, a pusher, slidably movable by elastic force, may be formed in a location corresponding to the pair of through-holes in the recess region, a removable button may be formed on the main body to control sliding movement of the pusher, and the pusher may be inserted into the through-hole to be fixed when the lower frame is seated in the recess region, and the pusher may be put out from the through-hole to remove the lower frame from the recess region when the removable button is pressed by external force.

In the 1-methylcyclopropene generation apparatus according to an embodiment of the present invention, at least one projection may be formed on a side surface of the recess region such that an external side surface of the lower frame is brought into close contact with the side surface of the recess region to be fixed thereto.

In the 1-methylcyclopropene generation apparatus according to an embodiment of the present invention, a rubber ring may be coupled to each of the lower portions of the pair of first tube connection terminals to maintain airtightness when the lower portions of the pair of first tube connection terminals are connected to the discharge terminal and the introduction terminal, respectively.

In the 1-methylcyclopropene generation apparatus according to an embodiment of the present invention, each of the discharge terminal and the introduction terminal may include a tube joint, into which the lower portion of the first tube connection terminal is inserted, and an elastic material disposed below the tube joint to apply force in an upward direction, and the tube joints may be configured such that upward movements thereof are limited by external frames of the discharge terminal and the introduction terminal, respectively.

The 1-methylcyclopropene generation apparatus according to an embodiment of the present invention may further include at least one magnetic material disposed inside the container and a magnetic motor disposed at the container and configured to apply magnetic force to the magnetic material such that the magnetic material is moved to mix materials accommodated in the container.

The 1-methylcyclopropene generation apparatus according to an embodiment of the present invention may further include a heating unit disposed at the container and configured to apply heat to the container in a state of being accommodated in the accommodation space of the main body.

The 1-methylcyclopropene generation apparatus according to an embodiment of the present invention may further include a circulation fan disposed at the main body and configured to facilitate diffusion of the reactant, comprising the 1-methylcyclopropene, discharged through the through-hole.

In the 1-methylcyclopropene generation apparatus according to an embodiment of the present invention, the container may include a container body and a container cap separably coupled an upper portion of the container body, and the pair of through-holes may be formed in an upper portion of the container cap, and an elastic material may be formed on an edge of each of the pair of through-holes to enhance airtightness.

Advantageous Effects

A 1-methylcyclopropene generation apparatus according to an embodiment of the present invention adopts a simple structure including a main body in which only a single container is mounted, and thus may be easily manufactured and easily used by a user without confusion of a container.

In addition, a separable cap is provided in an upper portion of the main body, allowing a user to easily generate 1-methylcyclopropene in a storehouse and resulting in easy maintenance.

Advantageous effects of the present invention are not limited to the above-description, and other various effects are included in this specification.

MODE FOR CARRYING OUT THE INVENTION

Figure 1:
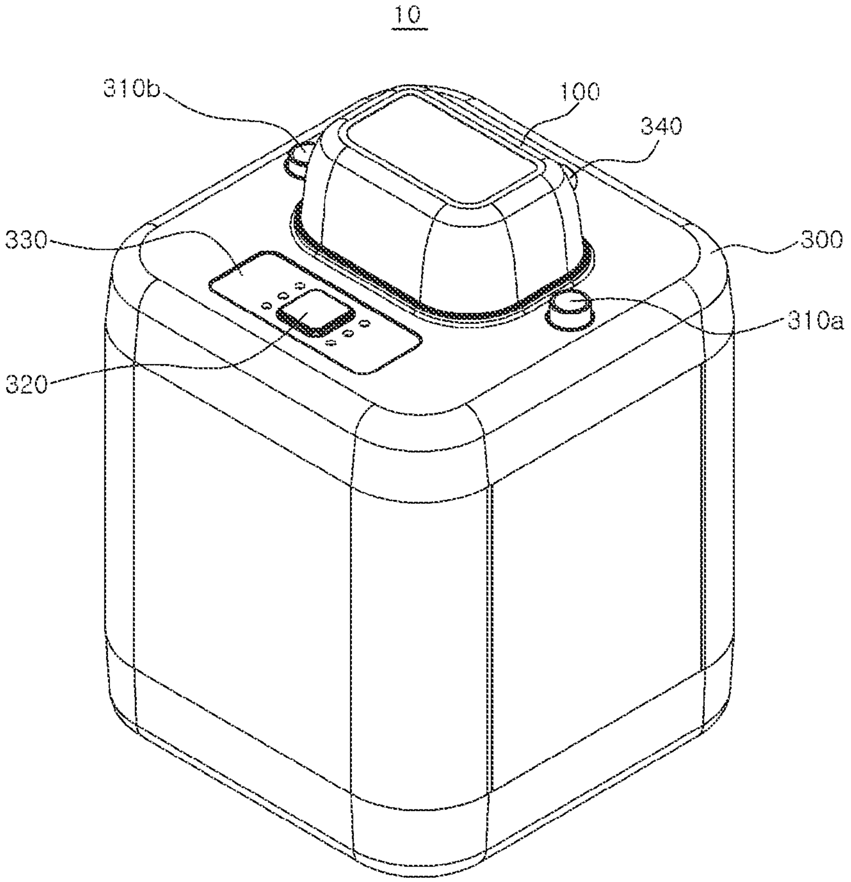
FIG. 1 is a perspective view of a 1-methylcyclopropene generation apparatus according to an embodiment of the present invention.

Various advantages and features of the present invention and methods accomplishing the same will become apparent from the following detailed description of embodiments with reference to the accompanying drawings. However, the present disclosure is not limited to the embodiments disclosed herein but will be implemented in various forms. The embodiments have made disclosure of the present invention complete and are provided so that those skilled in the art can easily understand the scope of the present invention. Therefore, the present invention will be defined by the scope of the appended claims. Like reference numerals throughout the description denote like elements.

Hereinafter, a 1-methylcyclopropene generation apparatus according to embodiments of the present invention will be described with reference to accompanying drawings.

Figure 2:
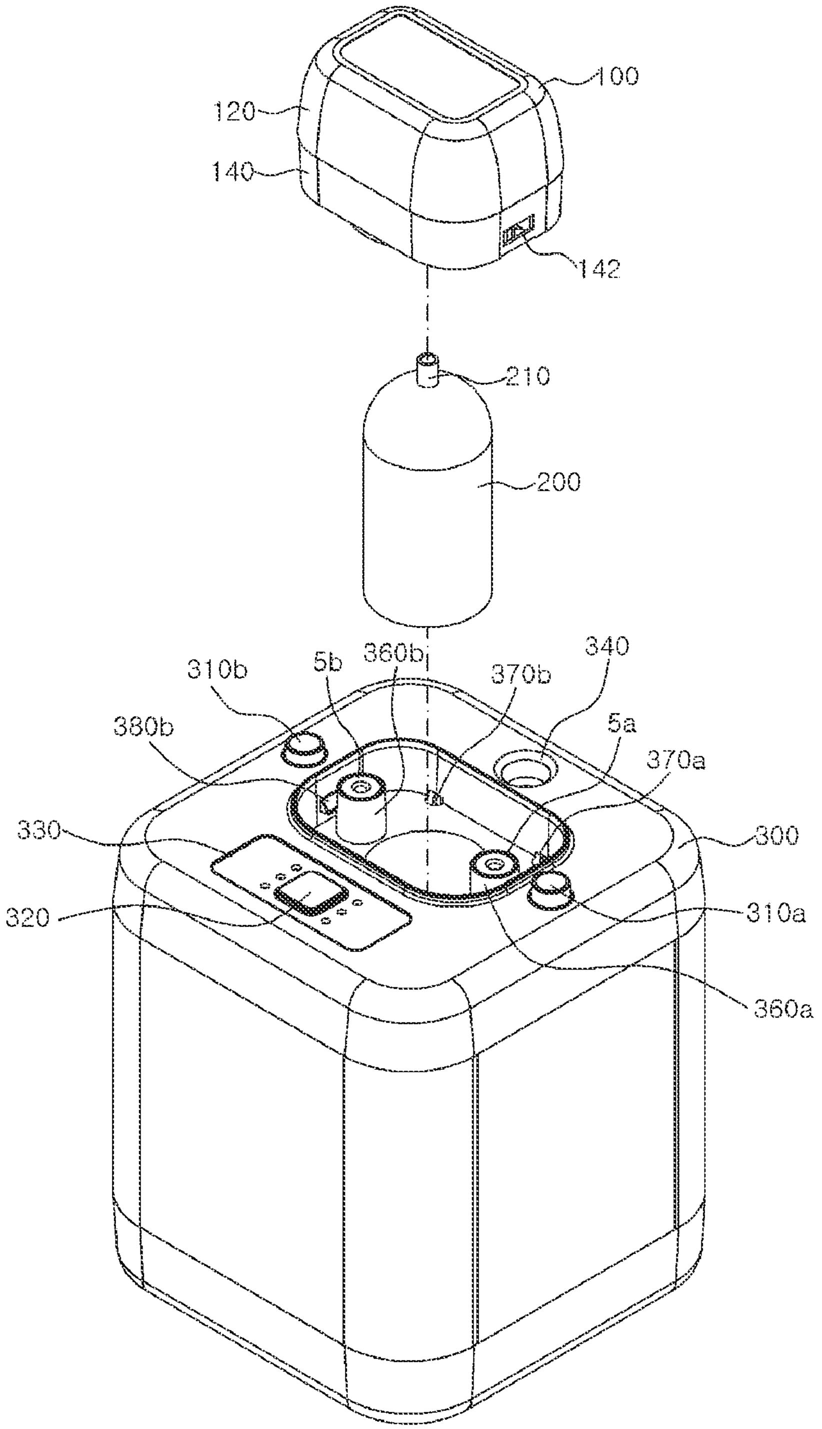
FIG. 2 is an exploded perspective view of the 1-methylcyclopropene generation apparatus according to an embodiment of the present invention.

FIG. 1 is a perspective view of a 1-methylcyclopropene generation apparatus according to an embodiment of the present invention, and FIG. 2 is an exploded perspective view of the 1-methylcyclopropene generation apparatus according to an embodiment of the present invention.

Referring to FIGS. 1 and 2, a 1-methylcyclopropene generation apparatus 10 according to an embodiment of the present invention may include a cap 100, a container 200, and a main body 300.

The container 200 may contain a 1-methylcyclopropene (1-MCP) precursor and a reaction solution, reacting with the 1-methylcyclopropene precursor to generate 1-methylcyclopropene, therein.

In this case, the reaction solution may be a fluorine anion-containing compound, and a mixed solution in the container 100 may be a solution in which an amount of the fluoride anion-containing compound solution is 1 to 5 equivalent weights based on 1 equivalent weight of the 1-methylcyclopropene precursor.

The fluoride anion-containing compound solution may be prepared by dissolving a fluoride anion-containing compound in a solvent. The solvent is not particularly limited as long as it dissolves the fluoride anion-containing compound. Specifically, the solvent may be a polar and aprotic solvent such as DMF, DMSO, dimethylacetamide, 1-methyl-2-pyrrolidone, or the like.

The 1-MCP precursor is in a liquid state, and thus may be used as it is without dissolving the 1-MCP precursor in a separate solvent. However, if there is a need to accurately produce a small amount of 1-MCP, the 1-MCP precursor may be diluted using a solvent and then used after accurately measuring the amount thereof.

In addition, a concentration of the fluoride anion-containing compound solution may be 5% to 65%, more preferably, 10% to 60%.

A material and a shape of the container 200 are not limited as long as the container has a structure allowing contained substances to be stably accommodated and to be discharged, as necessary. For example, the most widely used resins such as polyethylene and polypropylene may be used in terms of durability, lightweight, and economical costs, and a fluorinated resin such as Teflon may be also preferable in terms of durability, lightweight, handling convenience, and reliability of equipment.

In general, 1-MCP has a sufficient effect in air even at a low concentration of 1 ppm or less, so that approximately 0.275 to 19.25 g of a 60% diluted solution of the 1-MCP precursor and approximately 0.825 to 140 ml of a 20% diluted solution of the fluoride anion-containing compound are required to treat warehouses of 10 $m^3$ to 1,000 $m^3$. Accordingly, the container 200 used in the present invention may be a container having a capacity of approximately 200 ml. However, the present invention is not limited thereto, and the capacity of the container 200 may be selected within a range from 100 ml to 5000 ml depending on a capacity of a storehouse 100 and a size of the main body 300.

The container 200 may include a container body and a container cap 210 separably coupled to an upper portion of the container body. The container body may have a shape of a cylinder of which upper portion is opened, and the container cap 210 may be formed to have a shape of a hemisphere having a diameter decreased in an upward direction.

As will be described later in connection to FIG. 5, a pair of through-holes 210*a* and 210*b* may be formed in an upper portion of the container cap 210.

At least one magnetic material (not illustrated) may be disposed inside the container 200. The magnetic material may be a single magnetic bar or a plurality of magnetic bars, and may be rotated inside the container 200 by magnetic force, applied by a magnetic motor (not illustrated) disposed at the main body 300, to easily mix heterogeneous materials in the container 200.

The main body 300 may have an accommodation space for accommodating the container 200. A recess region for accommodating a portion of the cap 100 may be formed in the upper portion of the main body 300, and the accommodation space may be formed in a central portion of the recess region.

A discharge terminals 360*a* and an introduction terminals 360*b*, upwardly protruding from a bottom, may be formed on left and right sides of the accommodation space in the recess region.

As will be described later, when a compressor (not illustrated) operates under the control of a controller (not illustrated) installed at the main body 300, a carrier gas may be discharged through the discharge terminal 360*a*, the discharged carrier gas may pass through the inside of the container 200 via the cap, and a reactant inside the container 200 may be introduced back into the main body through the introduction terminal 360*b* by the carrier gas.

In the drawings, the recess region is illustrated as being formed to have a rectangular shape and the accommodation space is illustrated as having a cylindrical shape corresponding to the shape of the container 200, but this is only an example. The accommodation space may have another shape to correspond to the shape of the container 200, and the recess region may also have various other shapes such as a circular shape, an elliptical shape, or the like.

A power button 320 may be disposed on one side of an upper surface of the main body 300 to control turn-on and turn-off of the 1-methylcyclopropene generation apparatus 10. A display unit 330 may be disposed around the power button 320 to describe an operating state of the main body 300. Although only the power button 320 and the display unit 330 are illustrated in the drawings, buttons for various other controls such as a reset button or a test mode button may be formed, or the display unit 330 may be replaced with a touch panel.

A discharge hole 340 may be formed in the other side of the upper portion of the main body 300. The discharge hole 340 may serve to discharge a reactant, including 1-methylcyclopropene generated by mixing substances in the container 200, to an external entity.

The discharge hole 340 may be connected to the introduction terminal 360 by a pipe such as a tube to discharge the carrier gas and the reactant, introduced into the introduction terminal 360, to an external entity. Although the discharge hole 340 is illustrated as being formed in the upper portion of the main body 300, the discharge hole 340 may be formed in various locations such as a side surface of the main body 300, or the like.

In addition, although not illustrated, an air circulation outlet may be disposed adjacent to the discharge hole 340. A circulation fan may be disposed inside the air circulation outlet to facilitate diffusion of the reactant, including the 1-methylcyclopropene, discharge through the discharge hole 340.

A pair of removable buttons 360*a* and 360*b* may be disposed on the upper surface of the main body 300. A pair of pushers 380*a* and 380*b* may be disposed on a side surface of the recess region, and the pair of pushers 380*a* and 308*b* may be disposed to protrude from the side surface of the recess region. When the pair of removable buttons 360*a* and 360*b* are pressed by external force, the pair of pushers 380*a* and 380*b* may be slidably moved so as not to protrude from the side surface of the recess region by elastic force. A detailed operation thereof will be described later with reference to FIGS. 3 to 5.

The cap 100 may be coupled to the upper portion of the main body 300 in a state in which the container 200 is accommodated in the accommodation space of the main body 300. The cap 100 may be formed by coupling an upper frame 120 and a lower frame 140 to each other, and a pair of through-holes 142 for accommodating the pair of pushers 380*a* and 380*b* may be formed in one side and the other side of the lower frame 140.

The cap 100 may include a structure, such as a connection terminal and a tube, transferring the carrier gas, discharged from the discharge terminal 360*a* of the main body 300, into the container 200 and transferring the reactant, generated in the container 200, to the introduction terminal 360*b*, which will be described later with reference to FIGS. 3 to 5.

Projections 370*a* and 370*b* may be formed below the side surface of the recess region. Although not illustrated in FIG. 2, a pair of projections may also be formed on a side opposite to the region in which the projections 370*a* and 370*b* are formed.

The projections 370*a* and 370*b* may be brought into close contact with a side surface of the lower frame 140 of the cap 100 to serve to stably couple the cap 100 to the main body 300 when the cap 100 is accommodated in the recess region of the main body 300.

Figure 3:
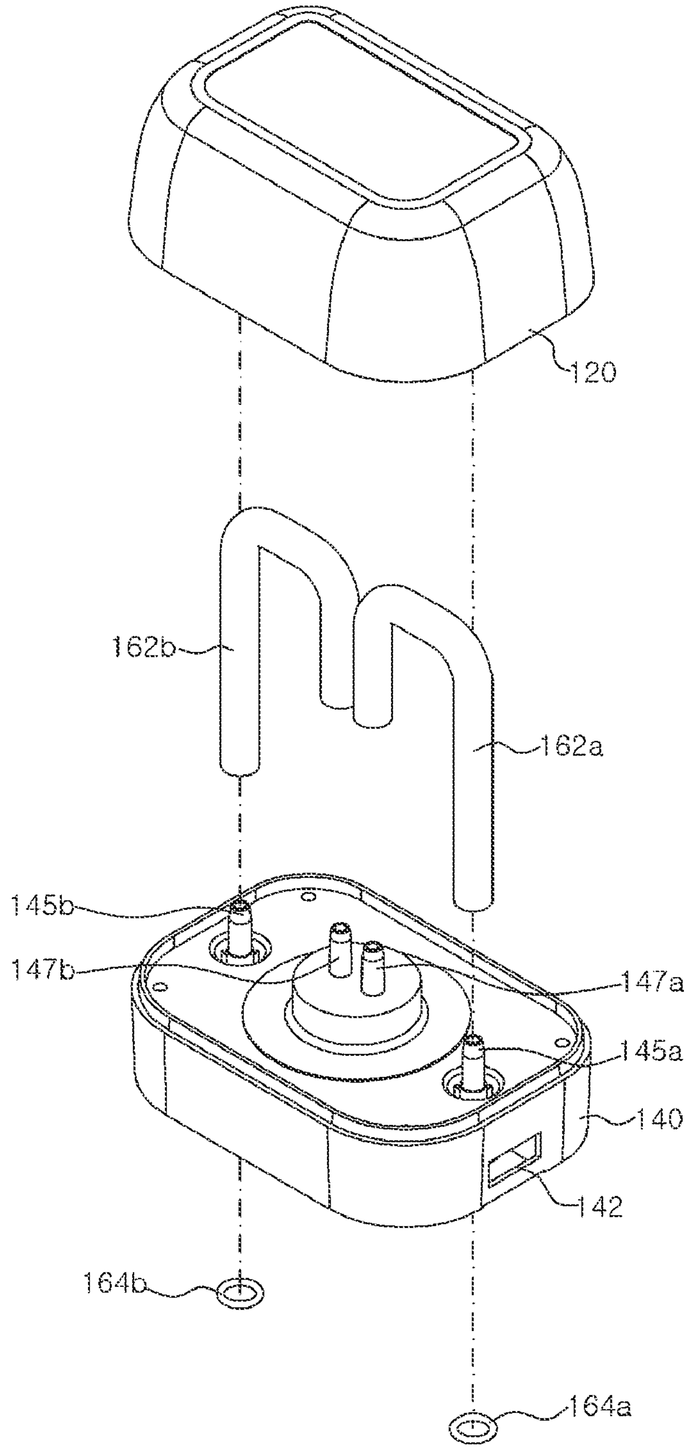
FIG. 3 is an exploded perspective view of a cap of the 1-methylcyclopropene generation apparatus according to an embodiment of the present invention.
Figure 4:
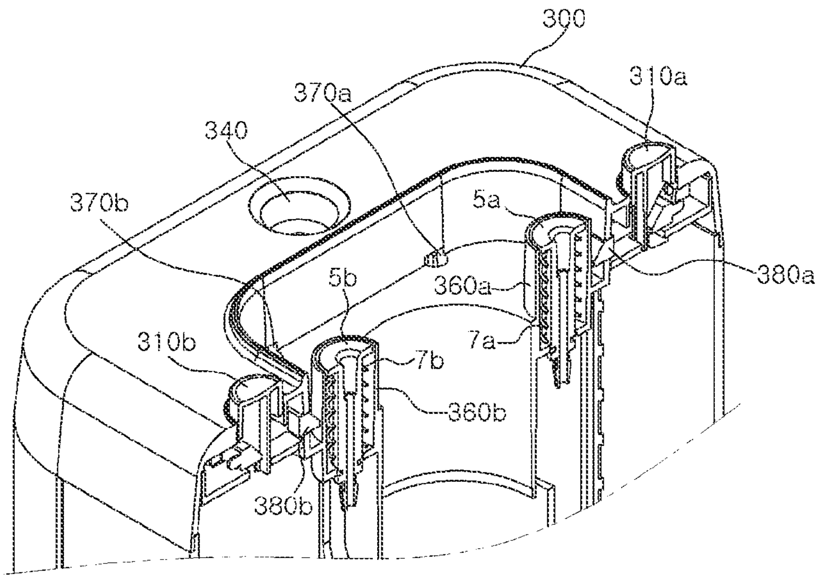
FIG. 4 is an exploded perspective view including a partial cross-section of a main body of the 1-methylcyclopropene generation apparatus according to an embodiment of the present invention.
Figure 5:
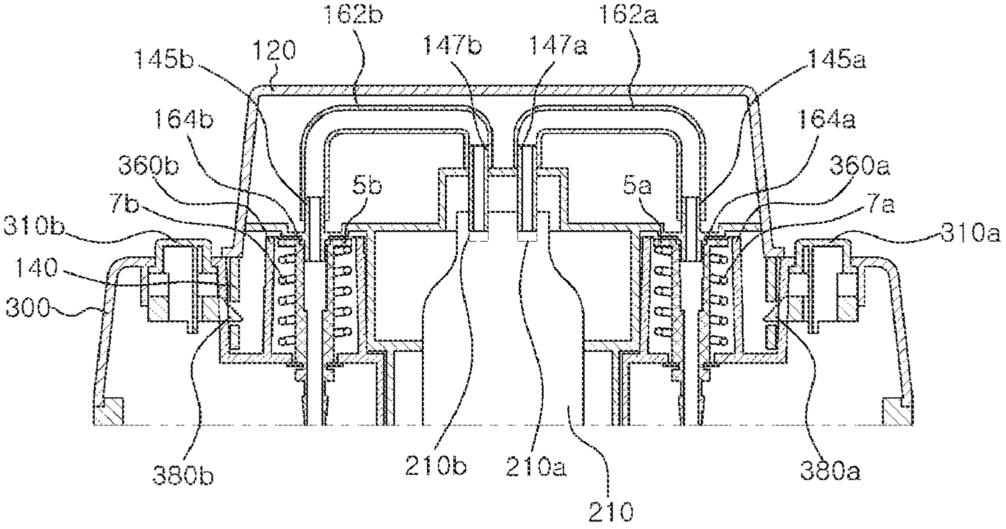
FIG. 5 is a partially cross-sectional view of the main body of the 1-methylcyclopropene generation apparatus according to an embodiment of the present invention.
Figure 6:
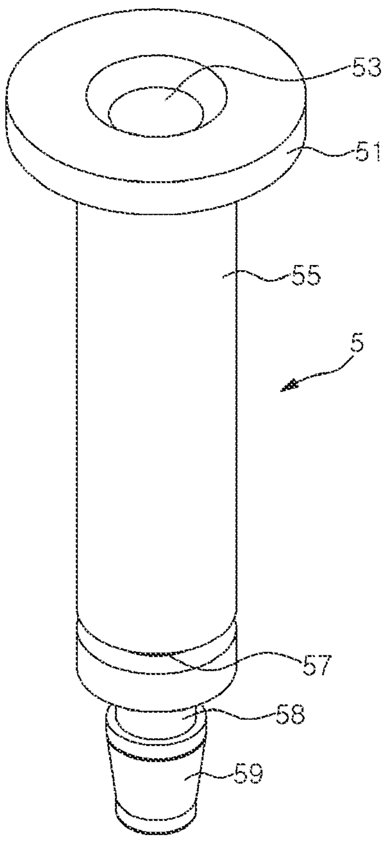
FIG. 6 is a perspective view of a tube joint applied to the 1-methylcyclopropene generation apparatus according to an embodiment of the present invention.

FIG. 3 is an exploded perspective view of a cap of the 1-methylcyclopropene generation apparatus according to an embodiment of the present invention, FIG. 4 is an exploded perspective view including a partial cross-section of a main body of the 1-methylcyclopropene generation apparatus according to an embodiment of the present invention, FIG. 5 is a partially cross-sectional view of the main body of the 1-methylcyclopropene generation apparatus according to an embodiment of the present invention, and FIG. 6 is a perspective view of a tube joint applied to the 1-methylcyclopropene generation apparatus according to an embodiment of the present invention.

The detailed structure and operation of the 1-methylcyclopropene generation apparatus 10 according to an embodiment of the present invention will be described with reference to FIGS. 3 to 6.

Referring to FIG. 3, the cap 100 may include an upper frame 120, a first tube 162*a*, a second tube 162*b*, a lower frame 140, and a pair of rubber rings 164*a* and 164*b*.

A pair of first tube connection terminals 145*a* and 145*b* may be formed on one side and the other side of the lower frame 140, and a pair of second tube connection terminals 147*a* and 147*b* may be formed in a central portion between the pair of first tube connection terminals 145*a* and 145*b*.

The first tube connection terminals 145*a* and 145*b* and the second tube connection terminals 145*a* and 145*b* may be formed to protrude upwardly and downwardly from an upper surface and a lower surface of the lower frame 140, respectively.

An upper protruding portion of each of the first tube connection terminals 145*a* and 145*b* may be connected to one side of each of the first tube 162*a* and the second tube 162*b*, and an upper protruding portion of each of the second tube connection terminals 147*a* and 147*b* may be connected to the other side of each of the first tube 162*b* and the second tube 162*b*.

In FIG. 3, a portion, in which the second tube connection terminals 147*a* and 147*b* are formed, of an upper surface of the lower frame 140 is formed to slightly protrude upwardly, so that a portion connecting the other sides of the first tube 162*a* and second tube 162*b* may be formed to have a length, smaller than a length of one side opposite thereto.

Lower protruding portions of the first tube connection terminals 145*a* and 145*b* may be coupled to the rubber rings 164*a* and 164*b*, respectively. The rubber rings 164*a* and 164*b* may serve to enhance airtightness when the first tube connection terminals 145*a* and 145*b* are coupled to the discharge terminal 360*a* and the introduction terminal 360*b* of the main body 300.

FIG. 4 is a perspective view including a cross-section of a central portion of the main body 300. In FIG. 4, the container 200 is not illustrated for brevity of illustration.

It may be identified that the pair of pushers 380*a* and 380*b* protrude to the side surface of the recess region of the main body through a through-hole formed in the side surface of the recess region. In an idle state, the pushers 380*a* and 380*b* may be disposed to protrude inwardly of the recess region through the through-hole formed in the side surface of the recess region, which may result from elastic force generated by an elastic material disposed inside the main body 300. The elastic material may be formed to have various structures such as a spring, an elastic plastic structure, or the like.

The elastic material may be connected to each of the pair of removable buttons 310*a* and 310*b*. When the removable buttons 310*a* and 310*b* are downwardly pressed by external force such as pressure applied by a user, the elastic material may be deformed, and thus the pushers 380*a* and 380*b* may be slidably moved to enter the through-hole so as not to protrude from the side surface of the recess region.

A cross-section of each of the pair of pushers 380*a* and 380*b* may be formed to have a tapered inclined surface formed such that left and right widths thereof are decreased in an upward direction. If they are formed as described above, when the lower frame 140 of the cap 100 is inserted into the recess region, a bottom surface of the lower frame 140 may press the inclined surfaces of each of the pushers 380*a* and 380*b* and the pushers 380*a* and 380*b* may be naturally moved into the through-hole formed on the side surface of the recess region by the pressing.

Accordingly, when the lower frame 140 is brought into contact with the bottom surface of the recess region, the pushers 380*a* and 380*b* may be automatically inserted again into the pair of through-holes 142 formed in the lower frame 140 by elastic force, and thus the cap 100 may be stably fixed to the recess region of the main body 300, as illustrated in FIG. 5.

When a user simultaneously presses the removable buttons 310*a* and 310*b* in the fixed state as illustrated in FIG. 5, the pair of pushers 380*a* and 380*b* may be moved into the through-hole of the recess region, so that the user may hold the upper frame 120 of the cap 100 and may separate the cap 100 from the main body 300.

In this case, although not illustrated, an elastic projection may be provided on a bottom surface of the recess region or a bottom surface of the lower frame 140 to facilitate the separation of the cap 100. The elastic projection may allow the cap 100 to automatically protrude upwardly when the user presses the removable buttons 310*a* and 310*b*.

Referring to FIGS. 4 and 5, a tube joint 5*a* and a tube joint 5*b* may be disposed on inner sides of external frames of the discharge terminal 360*a* and the introduction terminal 360*b*, respectively.

Referring to FIG. 6, the tube joint 5 may include a joint body 55, a joint cap 51 formed on an upper side of the joint body 55, and a joint end 59 formed on a lower side of the joint body 55.

A circular through-hole 53 may be formed in an upper portion of the joint cap 51 to provide a space into which first tube connection terminals 145*a* and 145*b* are inserted. The through-hole 53, formed in the upper portion of the joint cap 51, may extend to the joint body 55 and the joint end 59 overall to form a path through which a carrier gas or a reactive material passes.

The carrier gas may be an inert gas such as nitrogen, normal air, or the like.

A body recess 57 grooved to a predetermined depth may be formed on a lower end of the joint body 55, and an end recess 58 grooved to a predetermined depth may be formed on an upper side of the joint end 59.

Although not illustrated in the drawing, a tube connected from a compressor may be connected to the end recess 58, and may be coupled while allowing airtightness thereof to be maintained by an external side surface of the end recess 58 formed to be tapered and the end recess 58.

Referring to FIG. 5, the tube joints 5*a* and 5*b* may be disposed to be accommodated in frames of the discharge terminal 360*a* and the introduction terminal 360*b*. Specifically, the body recess 57 may be fitted with a frame of the main body 300, and a maximum movement range of an upper side of the joint cap 51 may be limited by upper frames of the discharge terminal 360*a* and the introduction terminal 360*b*.

Springs 7*a* and 7*b* may be coupled to joint bodies 55 of the tube joints 5*a* and 5*b*. The spring may allow upper surfaces of the joint caps 51 of the tube joints 5*a* and 5*b* to be brought into contact with upper frames of the discharge terminal 360*a* and the introduction terminal 360*b* by elastic force.

When the first tube connection terminal 145*a* and the second tube connection terminal 145*b* are inserted into through-holes of the joint caps 51 of the tube joints 5*a* and 5*b*, the joint caps 51 may be designed to be partially flexible in a downward direction by the spring. In this case, a vertical movement range may be determined by a vertical width of the body recess 57 formed on the joint body 55. For example, the vertical width of the body recess 57 may be designed such that a vertical flexible range is approximately 10 mm.

In addition, as illustrated in FIG. 6, a surface connected to the through-hole 53 from the upper surface of the joint cap 51 may be formed as a tapered inclined surface of which diameter is decreased in a direction toward a center.

As illustrated in FIG. 5, the first tube connection terminals 145*a* and 145*b* may be coupled to the tube joints 5*a* and 5*b* while the O-ring type rubber rings 164*a* and 164*b* are coupled to the first tube connection terminals 145*a* and 145*b*, the rubber ring 164*a* and 164*b* may be brought into contact with the tapered inclined surfaces of the joint caps 51 to maintain airtightness, respectively.

In addition, referring to FIG. 5, a structure in which the container cap 210 of the container 200 is connected to the second tube connection terminals 147*a* and 147*b* may be identified. Specifically, a pair of through-holes 210*a* and 210*b* may be formed in an upper surface of the container cap 210, and the second tube connection terminals 147*a* and 147*b* may be inserted into the pair of through-holes 210*a* and 210*b*.

That is, when the user presses the upper frame 120 of the cap 100 and inserts the upper frame 120 of the cap 100 into the recess region of the upper portion of the main body 300, the bottom surface of the lower frame 140 may be brought into contact with the bottom surface of the recess region while the pair of pushers 380*a* and 380*b* are inserted into a through-hole, formed in a side surface of the recess region, by the pressed force.

When the bottom surface of the lower frame 140 is brought into contact with the bottom surface of the recess region, the pair of pushers 380*a* and 380*b* may protrude outwardly of the through-hole in the side surface of the recess region and be inserted into the pair of through-holes of the lower frame 140 to stably fix the cap 100 to the main body 300.

In this case, when the cap 100 is coupled to the main body 300, the first tube connection terminals 145*a* and 145*b* are inserted into and coupled to the discharge terminal 360*a* and the introduction terminal 360*b* of the main body 300, and the second tube terminals 147*a* and 147*b* may be inserted into and coupled to the pair of through-holes 210*a* and 210*b* of the container 200 disposed in the accommodation space of the main body 300.

In this case, an element such as an elastic film formed of an elastic material may be additionally formed on edges of the pair of through-holes 210*a* and 210*b* to enhance the airtightness.

When the user presses a power button 320 in the coupled state as illustrated in FIG. 5, a control unit disposed inside the main body 300 may operate the compressor to inject carrier gas into the through-hole of the joint end 59 of the tube joint 5*a*.

The injected carrier gas may pass through the through-hole 53 of the tube joint 5*a* and may be injected into the through-hole 210*a* of the container 200 through the first tube 162*a*.

The carrier gas injected into the through-hole 210*a* may discharge the reactant, containing 1-methylcyclopropene generated by a reaction between the 1-methylcyclopropene precursor and the reactive material mixed in the container 200, through the through-hole 210*b* to be transferred to the introduction terminal 360*b* through the second tube 162*b*.

The carrier gas and the reactant, transferred through the through-hole of the tube joint 5*b* of the introduction terminal 360*b*, may be discharged through the through-hole 340 via a connection pipe (not illustrated), such as a tube, connected to the joint end 59 of the tube joint 5*b*.

In this case, prior to the operating the compressor to circulate the carrier gas, mixing materials in the container 200 and heating the container 200 may be performed to promote the reaction of the materials in the container 200.

The mixing the materials in the container 200 may be performed by applying magnetic force, applied by a magnetic motor, to at least one magnetic bar disposed in the container 200 to rotate the magnetic bar.

The heating the container 200 may be performed by applying heat to the accommodation space through a heating element (not illustrated) disposed inside the body 300. In this case, heating temperature may be set between 10 degrees and 60 degrees, preferably between 20 degrees and 50 degrees.

Figure 7:
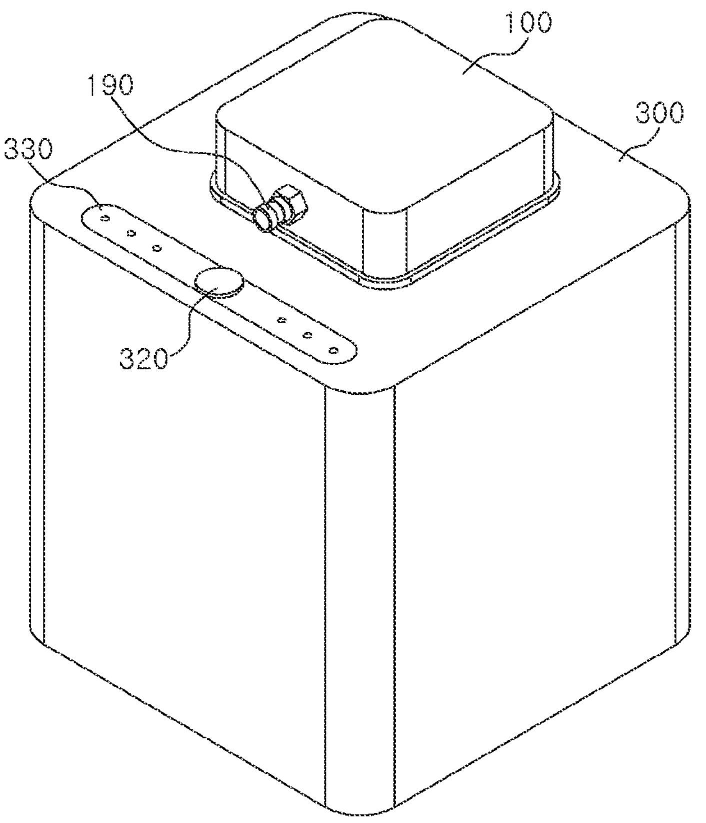
FIG. 7 is a perspective view of a 1-methylcyclopropene generation apparatus according to anther embodiment of the present invention.

FIG. 7 is a perspective view of a 1-methylcyclopropene generation apparatus according to anther embodiment of the present invention.

In the embodiment of FIG. 7, unlike the embodiment of FIGS. 1 to 6, a discharge terminal 190 for discharging a reactant may be formed at a cap 100, rather than a main body 300.

In this case, only a discharge terminal may be formed at a main body 300 and an introduction terminal may be omitted. There may be provided a structure in which a tube, connected to a through-hole through which a reactant generated in a container is discharged, is connected to the discharge terminal 190.

Except for the above-described differences, other structures in which a power button 320 and a display unit 330 are provided at the main body 300 are the same, so that detailed descriptions thereof are omitted.

The foregoing description of the present invention is intended for exemplifications, and it will be understood by those skilled in the art that the present invention may be easily modified in other specific forms without changing the technical idea and or essential features of the present invention. Therefore, it should be understood that the embodiments described above are exemplary in all aspects and not restrictive. For example, each component described as a single type may be implemented in a distributed manner, and similarly, components described as distributed may be implemented in a combined form. The scope of the present invention is shown by the following claims rather than the above description, and all changes or modifications derived from the meaning and scope of the claims and their equivalents should be construed as being included in the scope of the present invention.

The invention claimed is:

1. A 1-methylcyclopropene generation apparatus comprising: a container, a 1-methylcyclopropene (1-MCP) precursor, and a reaction solution, reacting with the 1-methylcyclopropene precursor to generate 1-methylcyclopropene, therein and having a pair of through-holes formed on an upper portion thereof; a main body comprising an accommodation space for accommodating the container; and a cap coupled to the upper portion of the main body in a state in which the container is accommodated in the accommodation space of the main body, wherein a recess region for accommodating a portion of the cap is formed in the upper portion of the main body, and a discharge terminal and an introduction terminal protruding upwardly are formed in the recess region, the cap comprises an upper frame, a lower frame, and a first tube and a second tube disposed between the upper frame and the lower frame, the lower frame comprises a pair of first tube connection terminals, disposed on one side and the other side, and a pair of second tube connection terminals disposed between the pair of first tube connection terminals, upper portions of the pair of first tube connection terminals are connected to one side of the first tube and one side of the second tube, upper portions of the pair of second tube connection terminals are connected to the other side of the first tube and the other side of the second tube, lower portions of the pair of first tube connection terminals are connected to the discharge terminal and the introduction terminal, respectively, the lower portions of the pair of second tube connection terminals are connected to the pair of through-holes, respectively, the introduction terminal is connected to a discharge hole formed in an outer side of the main body, and the 1-methylcyclopropene generation apparatus comprises a control unit configured to discharge a carrier gas to the discharge terminal to discharge a reactant, comprising the 1-methylcyclopropene generated in the container, through the discharge hole.

2. The 1-methylcyclopropene generation apparatus of claim 1, wherein complementary coupling elements are formed at the lower frame of the cap and the recess region of the main body such that the lower frame is accommodated in the recess region to be stably coupled thereto.

3. The 1-methylcyclopropene generation apparatus of claim 2, wherein a pair of through-holes are formed in a side surface of the lower frame, a pusher, slidably movable by elastic force, is formed in a location corresponding to the pair of through-holes in the recess region, a removable button is formed on the main body to control sliding movement of the pusher, and the pusher is inserted into the through-hole to be fixed when the lower frame is seated in the recess region, and the pusher is put out from the through-hole to remove the lower frame from the recess region when the removable button is pressed by external force.

4. The 1-methylcyclopropene generation apparatus of claim 2, wherein at least one projection is formed on a side surface of the recess region such that an external side surface of the lower frame is brought into close contact with the side surface of the recess region to be fixed thereto.

5. The 1-methylcyclopropene generation apparatus of claim 2, wherein a rubber ring is coupled to each of the lower portions of the pair of first tube connection terminals to maintain airtightness when the lower portions of the pair of first tube connection terminals are connected to the discharge terminal and the introduction terminal, respectively.

6. The 1-methylcyclopropene generation apparatus of claim 2, wherein each of the discharge terminal and the introduction terminal comprises a tube joint, into which the lower portion of the first tube connection terminal is inserted, and an elastic material disposed below the tube joint to apply force in an upward direction, and the tube joints are configured such that upward movements thereof are limited by external frames of the discharge terminal and the introduction terminal, respectively.

7. The 1-methylcyclopropene generation apparatus of claim 2, further comprising:

at least one magnetic material disposed inside the container; and a magnetic motor disposed at the container and configured to apply magnetic force to the magnetic material such that the magnetic material is moved to mix materials accommodated in the container.

8. The 1-methylcyclopropene generation apparatus of claim 7, further comprising:

a heating unit disposed at the container and configured to apply heat to the container in a state of being accommodated in the accommodation space of the main body.

9. The 1-methylcyclopropene generation apparatus of claim 2, further comprising:

a circulation fan disposed at the main body and configured to facilitate diffusion of the reactant, comprising the 1-methylcyclopropene, discharged through the through-hole.

10. The 1-methylcyclopropene generation apparatus of claim 2, wherein the container comprises a container body and a container cap separably coupled an upper portion of the container body, and the pair of through-holes are formed in an upper portion of the container cap, and an elastic material is formed on an edge of each of the pair of through-holes to enhance airtightness.

* * * * *